United States Patent [19]

Hackl et al.

[11] Patent Number: 5,360,601
[45] Date of Patent: Nov. 1, 1994

[54] PROCESS FOR THE PREPARATION OF ISOCYANIC ACID BY THE DECOMPOSITION OF N,N-DISUBSTITUTED UREAS

[75] Inventors: Kurt A. Hackl; Martin Müllner, both of Linz; Erich Schulz, Ansfelden; Gerhard Stern, Sonnberg; Heinz Falk, Linz, all of Austria

[73] Assignee: Chemie Linz Gesellschaft m.b.H., Austria

[21] Appl. No.: 105,672

[22] Filed: Aug. 13, 1993

[30] Foreign Application Priority Data

Aug. 13, 1992 [AT] Austria ................... 1630/92

[51] Int. Cl.⁵ ............................................. C01B 21/12
[52] U.S. Cl. ..................... 423/364; 423/365; 560/330; 560/344
[58] Field of Search ............... 423/365, 364; 560/344, 560/330

[56] References Cited

U.S. PATENT DOCUMENTS

| | | | |
|---|---|---|---|
| 3,314,754 | 4/1967 | Godfrey | 423/364 |
| 3,936,484 | 2/1976 | Rosenthal et al. | 560/344 |
| 3,970,742 | 7/1976 | Verstegen | 423/365 |
| 5,043,444 | 8/1991 | Müllner et al. | 544/169 |
| 5,078,980 | 1/1992 | Müllner et al. | 423/263 |
| 5,124,451 | 6/1992 | Hackl et al. | 544/169 |
| 5,169,954 | 12/1992 | Hackl et al. | 544/169 |

OTHER PUBLICATIONS

Chemical Abstracts, 102:46723r (1985), "Method and Apparatus for Preparing a Cyanuric Acid-Poor Isocyanic Acid-ammonia Gas Mixture".
Chemical Abstracts, 104:88146b (1986), "Fluidized Bed Reactor and Method for Producing Low-Cyanuric Acid Isocyanic Acid-Ammonia Gas Mixtures".
Chemical Abstracts, vol. 81: 172444m (1974), "Isocyanic Acid From Urea".
Chemical Abstracts, 82: 173135u (1974), "Isocyanic Acid".
Chemical Abstracts, 116:109513j (1992), "Manufacture of Liquid Isocyanic Acid".

Primary Examiner—José G. Dees
Assistant Examiner—Dwayne C. Jones
Attorney, Agent, or Firm—Wenderoth, Lind & Ponack

[57] ABSTRACT

A process for the preparation of isocyanic acid, characterized in that N,N-disubstituted ureas are decomposed at elevated temperature to a secondary amine of lower volatility and to isocyanic acid, which is drawn off at the top.

6 Claims, No Drawings

PROCESS FOR THE PREPARATION OF ISOCYANIC ACID BY THE DECOMPOSITION OF N,N-DISUBSTITUTED UREAS

SCOPE OF THE INVENTION

The invention relates to a process for the preparation of isocyanic acid by the decomposition N,N-disubstituted ureas.

BACKGROUND OF THE INVENTION

By virtue of its high reactivity, isocyanic acid represents a valuable C-1 structural unit for the synthesis of a large number of compounds.

It can be prepared according to EP-A-0 124 704 by heating molten urea in a fluidized bed to give an isocyanic acid/ammonia mixture. However, isolation of the isocyanic acid from this mixture presents difficulties because ammonium isocyanate, which very readily isomerizes to urea again, is formed when the ammonia/isocyanic acid mixture cools.

The thermal decomposition of urea with the elimination of ammonia is known from Chemical Abstracts, vol. 81 (1974) 172444m and vol. 82 (1975) 173135u, but a solid, namely cyanuric acid, is formed which has to be decomposed to isocyanic acid at 330° to 600° C. The decomposition proceeds only slowly and not to completion. Although EP-A-0 416 236 describes improved processes for the separation of ammonia from isocyanic acid/ammonia mixtures by the addition of tertiary amines or ethers, the object of the present invention was to find a novel process for the preparation of isocyanic acid which is easy to carry out and in which isocyanic acid is obtained in high yield and purity without a subsequent separation step.

SUMMARY OF THE INVENTION

The invention accordingly relates to a process for the preparation of isocyanic acid which is characterized in that N,N-disubstituted ureas are decomposed at elevated temperature to a secondary amine of lower volatility and to isocyanic acid, which is drawn off at the top.

DETAILED DESCRIPTION OF THE INVENTION

In principle, suitable starting compounds for the preparation of isocyanic acid by the process according to the invention are any N,N-disubstituted ureas which decompose under thermal stress to isocyanic acid and to a secondary amine of lower volatility.

Preferred N,N-disubstituted ureas are those of formula I

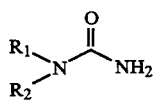

in which $R_1$ and $R_2$ are identical or different anti are a linear, branched or cyclic $(C_1-C_{24})$-alkyl radical which is unsubstituted or substituted by $(C_1-C_6)$-alkoxy or phenyl, or a phenyl radical which is unsubstituted or substituted by $(C_1-C_6)$-alkyl, $(C_1-C_6)$-alkoxy, hydroxyl, halogen such as chlorine or bromine, nitro or amino.

Examples of alkyl radicals are methyl, ethyl propyl, isopropyl, butyl, sec-butyl, tert-butyl hexyl, octyl, decyl, dodecyl, hexadecyl, octadecyl, cyclohexyl or cycloheptyl radicals. Examples of $(C_1-C_6)$-alkoxy radicals are methoxy, ethoxy, propoxy, butoxy or hexyloxy. Examples of substituted phenyl radicals are tolyl, aminophenyl or chlorophenyl radicals.

Examples of particularly preferred starting compounds are N,N-dibutylurea, N,N-dihexylurea, N,N-dioctylurea, N,N-didodecylurea, N,N-dihexadecylurea, N,N-dioctadecylurea, N,N-dicyclohexylurea and N,N-dibenzylurea. The substituted ureas can be prepared for example via the N-alkylation of urea, as described in European Patent 0 471 983.

The substituted ureas can be used in liquid or as a melt, without the use of a diluent.

However, the decomposition can also be carried out in a diluent which is inert under the reaction conditions, suitable diluents being aliphatic or aromatic hydrocarbons such as, for instance, dodecane, hexadecane, octadecane, toluene and xylenes, ethers such as e.g. diethylene glycol dibutyl ether, paraffins or mixtures thereof. It is preferable to use hexadecane and diethylene glycol dibutyl ether.

However, the amine formed by the decomposition of the urea can also be used as the diluent.

A further possibility is also to add to the reaction mixture a solvent for the isocyanic acid which prevents the isocyanic acid from polymerizing or stabilizes the isocyanic acid by complexation, and then, when the reaction has ended, condenses in the cold trap together with the isocyanic acid to give a clear solution of pure isocyanic acid which is easy to handle. Examples of solvents for the isocyanic acid are aliphatic or aromatic hydrocarbons which can optionally also be halogenated, such as, for instance, chloroform, methylene chloride, toluene and xylenes, and ethers such as, for instance, tetrahydrofuran, dioxane, diisopropyl ether, diethyl ether, tert-butyl methyl ether, diethoxyethane, dimethoxyethane, diethylene glycol dialkyl ethers or triethylene glycol alkyl ethers, with the restriction that the boiling point of the solvent is not higher than the reaction temperature used. However, it is preferable to add toluene or an ether such as diethylene glycol dibutyl ether, diethyl ether, diethoxyethane or dimethoxyethane. The amount of solvent added here is such that the concentration of the solution of isocyanic acid obtained in the cold trap is at most 10%.

The reaction temperature is between about 90° and 400° C., preferably between about 150° and 300° C. and particularly preferably between 180° and 260° C., depending on the urea used.

The isocyanic acid formed can be isolated in several ways.

Thus, for example, it suffices to distil off the isocyanic acid or the isocyanic acid/solvent mixture and condense it in a cold trap cooled with liquid nitrogen, or absorb it in one of the suitable solvents mentioned above, whose boiling point can however also be above the reaction temperature.

To improve the separation of secondary amine and isocyanic acid, it is also possible to use a fractionation column, whereby any entrained amine is washed back into the reaction mixture by the condensing diluent, or the isocyanic acid ,is removed from the reaction mixture by means of a stream of inert gas, for instance by means of a stream of nitrogen or a stream of $CO_2$.

The procedures which have just been mentioned for the isolation of the isocyanic acid can be applied individually or else in combination.

The above-mentioned process variants can be carried out either batchwise or continuously, e.g. in a thin film evaporator or in a packed column.

Isocyanic acid is obtained in high yields and high purity by this process. The isocyanic acid obtained in this way can then either be stored for a few weeks at temperatures of −80° C. to −20° C., in the pure form or as a solution, or be absorbed in a solvent and immediately processed further by the addition of the appropriate reactant.

The secondary amine, which is formed as the second product of the decomposition, can be purified for example by distillation under reduced pressure and used as a starting compound for a variety of reactions, or the bottom product, which contains not only the secondary amine but also small amounts of unreacted substituted urea and, if appropriate, a diluent, can be re-used directly, without further working-up, for the preparation of new substituted ureas, for instance according to European Patent 410 168.

EXAMPLE 1

Batch Preparation of Isocyanic Acid

A 2% solution (1 g/49 g of diluent) of dibenzylurea in hexadecane was placed in a suitable apparatus consisting of a flask with inlet facilities for the inert gas and the additional solvent for the isocyanic acid, a thermometer, an attached, heatable, 20 cm long Vigreux column and an ordinary condenser, and the solution was; heated to 200° C. with the simultaneous introduction of a stream of nitrogen (17 l/h). Diethyl ether was additionally metered into the bottom (80 ml/h).

The isocyanic acid formed and the diethyl ether were absorbed in a gas-washing bottle cooled with ice-water and charged with diethyl ether.

To determine the yield, the organic phase from the gas-washing bottle was extracted with water and the content of isocyanic acid was titrated potentiometrically with $AgNO_3$, or the organic phase was extracted with aqueous NaOH and the excess NaOH was back-titrated with HCl.

Yield: 86%

The following Examples were carried out analogously to Example 1:

TABLE 1

| Urea | Diluent | Conc. of solution (% by weight) | T (°C.) | $N_2$ flow | Solvent for isocyanic acid | Yield (%) |
| --- | --- | --- | --- | --- | --- | --- |
| 2. dibenzyl-urea | hexadecane | 5 | 250 | 7 l/h | diethyl ether 40 ml/h | 57 |
| 3. dibenzyl-urea | hexadecane | 10 | 200 | 17 l/h | diethyl ether 80 ml/h | 50 |
| 4. dibenzyl-urea | hexadecane | 5 | 200 | 17 l/h | diethyl ether 40 ml/h | 69 |
| 5. dibenzyl-urea | hexadecane | 5 | 200 | 34 l/h | — | 69 |
| 6. dibenzyl-urea | hexadecane | 5 | 200 | 17 l/h | diethoxyethane 80 ml/h | 80 |
| 7. Dioctyl-urea | hexadecane | 5 | 200 | 17 l/h | diethyl ether 80 ml/h | 65 |

EXAMPLE 8

Continuous Preparation in a Thin Film Evaporator

A 5% by weight solution of dioctylurea in hexadecane was metered over 1 hour into a thin film evaporator maintained at a temperature of 230° C. The flow rate of inert gas in the thin film evaporator was 17 l/h of $N_2$. The isocyanic acid formed was absorbed in a receiver cooled with water (15° C.) and charged with 50 ml of toluene.

To determine the yield, the toluene solution was extracted with sodium hydroxide solution and the content of isocyanic acid was determined by back titration with hydrochloric acid.

Yield: 50%

EXAMPLE 9

Continuous Preparation in a Packed Column

A packed column charged with Raschig rings and fitted with an ordinary condenser was heated to 250° C. and a 5% by weight solution of dioctylurea in hexadecane was introduced into the top (10 ml/h). 17 l/h of $N_2$ were introduced into the bottom. The stripper gas and the isocyanic acid formed were cooled to room temperature in the condenser and absorbed in a gas-washing bottle filled with diethyl ether and cooled with ice-water.

The yield was determined analogously to Example 8.

Yield: 86%

EXAMPLE 10

The procedure was analogous to Example 9.

5% by weight solution of dioctylurea in diethylene glycol dibutyl ether, charge rate 10 ml/h, 5 l/h of $N_2$, reaction temperature 200° C.

Yield: 48%

EXAMPLE 11

The procedure was analogous to Example 9.

5% by weight solution of dibenzylurea in diethylene glycol dibutyl ether, charge rate 20 ml/h, 80 ml/h of diethyl ether as solvent for isocyanic acid, 17 l/h of $N_2$, reaction temperature 200° C.

Yield: 75%

EXAMPLE 12

The procedure was analogous to Example 9.

5% by weight solution of dioctylurea in diethylene glycol dibutyl ether, charge rate 10 ml/h, 17 l/h of $N_2$, 80 ml/h of diethylene glycol dibutyl ether as solvent for isocyanic acid, reaction temperature 240° C.

Yield: 80%

EXAMPLE 13

The procedure was analogous to Example 9.

10% by weight solution of dioctylurea in diethylene glycol dibutyl ether, charge rate 20 ml/h, 80 ml/h of diethylene glycol dibutyl ether as solvent for isocyanic acid, 17 l/h of $N_2$, reaction temperature 240° C.

Yield: 68%

What we claim is:

1. A process for the preparation of isocyanic acid, which comprises decomposing an N,N-disubstituted urea in a reaction vessel at elevated temperature to a secondary amine of lower volatility and to isocyanic acid, which is drawn off at the top of said vessel.

2. The process according to claim 1, wherein the N,N-disubstituted ureas used are those of the formula I:

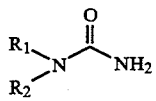

in which $R_1$ and $R_2$ are identical or different and are a linear, branched or cyclic $(C_1-C_{24})$-alkyl radical which is unsubstituted or substituted by $(C_1-C_6)$-alkoxy or phenyl, or a phenyl radical which is unsubstituted or substituted by $(C_1-C_6$-alkyl, $(C_1-C_6$-alkoxy, hydroxyl, halogen, nitro or amino.

3. The process according to claim 1, wherein the N,N-disubstituted ureas used are those of formula I in which $R_1$ and $R_2$ are a linear, branched or cyclic $(C_4-C_{20})$-alkyl radical or a benzyl radical.

4. The process according to claim 1 wherein the decomposition of the urea is carried out without a diluent or in a diluent which is inert under the reaction conditions, optionally in combination with a solvent for the isocyanic acid and/or with a stream of inert gas.

5. The process according to claim 1, wherein the reaction temperature is about 150° to 300° C.

6. The process according to claim 1, wherein the reaction temperature is about 180° to 260° C.

* * * * *